United States Patent [19]

White

[11] Patent Number: 4,554,918
[45] Date of Patent: Nov. 26, 1985

[54] OCULAR PRESSURE RELIEF DEVICE

[76] Inventor: Thomas C. White, 1127 Holly Dr., Sioux Falls, S. Dak. 55705

[21] Appl. No.: 402,774

[22] Filed: Jul. 28, 1982

[51] Int. Cl.$^4$ ................... A61M 27/00; A61F 1/00
[52] U.S. Cl. .................................... 604/10; 623/6
[58] Field of Search ........................ 604/8–10, 604/247; 128/350 V, 1 R; 3/1

[56] References Cited

U.S. PATENT DOCUMENTS

| | | | |
|---|---|---|---|
| 555,588 | 3/1896 | Spencer | 604/247 |
| 2,969,066 | 1/1961 | Holter et al. | 128/350 |
| 3,452,757 | 7/1969 | Ames | 604/8 |
| 3,542,026 | 11/1970 | Beldsoe | 604/247 |
| 3,726,284 | 4/1973 | Parker | 604/8 |
| 3,788,327 | 1/1974 | Donowitz et al. | 604/9 |
| 3,827,439 | 8/1974 | Schulte et al. | 604/9 |
| 4,240,434 | 12/1980 | Newkirk | 128/350 |

OTHER PUBLICATIONS

Zorab, A., The Reduction of Tension in Chronic Glaucoma, Ophthalmoscope, 1:258–261, 1912.
Stefansson, J., An Operation for Glaucoma, Am. J. Ophth., 8:681–693, 1925.
Wolfe, O. and Blaess, M., Seton Operation in Glaucoma, Am. J. Ophth. 19:400–406, 1936.
Bick, M., Use of Tantalum for Ocular Drainage, Arch. Ophth. 42:373–388, 1949.
Muldoon, et al., Platinum Implant in Glaucoma Surgery, Arch. Ophth. 45:666–672, 1951.
Laval, J., The Use of Absorbable Gelatin Film (Gelfilm) in Glaucoma Filtration Surgery, A.M.A. Arch. Ophth. 54:677–682, 1955.
Carrington, K., Ventriculo-Venous Shunt Using the Holter Valve as a Treatment of Hydrocephalus, JMSMS Mar. 1959, pp. 373–376, 383.
Ellis, R., Reduction of Interocular Pressure Using Plastics in Surgery, Am. J. Ophth. 50:733–743, 1960.
Ore, S., et al., Preparation of Surgical Implants from Silicone Rubber by Means of a Postforming Technique, Surgery 52:385–389, 1962.
Lee, P. and Schepens, C., Aqueous-Venous Shunt and Intraocular Pressure, Preliminary Report of Animal Studies, Invest. Ophth. 5:59–63, 1966.
Welkowicz, M. et al., Gold Leaf Seton for Lowering Intraocular Pressure, Ann. Ophthal. 3:527–541, 1971.
Krejci, L., Microdrainage of Anterior Chamber of Eye Glaucoma Operation Using Hydron Capillary Drain, Acta. Univ. Carol. Med. Monographia LXI, 1974.
Krupin, T. et al., Valve Implants in Filtering Surgery, Am. J. Ophthal., 81: 232–235, 1976.
Molteno, A. et al., Implants for Draining Neovascular Glaucoma. Brit. J. Ophth. 61:120–125, 1977.

Primary Examiner—Richard J. Apley
Assistant Examiner—David J. Isabella
Attorney, Agent, or Firm—James R. Haller; Gregory P. Kaihoi

[57] ABSTRACT

A prosthetic device for the relief of high intraocular pressures associated with glaucoma is shown. The device includes a limp reservoir adapted to be worn against or within the eye wall, a conduit leading from the reservoir to the anterior chamber of the eye, and means for communicating the reservoir with liquid-receptive tissue. Unidirectional flow means, such as a check valve, is employed to prevent back-flow of liquid into the anterior chamber. When the reservoir is periodically compressed, aqueous humor collected in the reservoir is expelled into liquid-receptive tissue where it is absorbed or is passed to the venous system.

13 Claims, 8 Drawing Figures

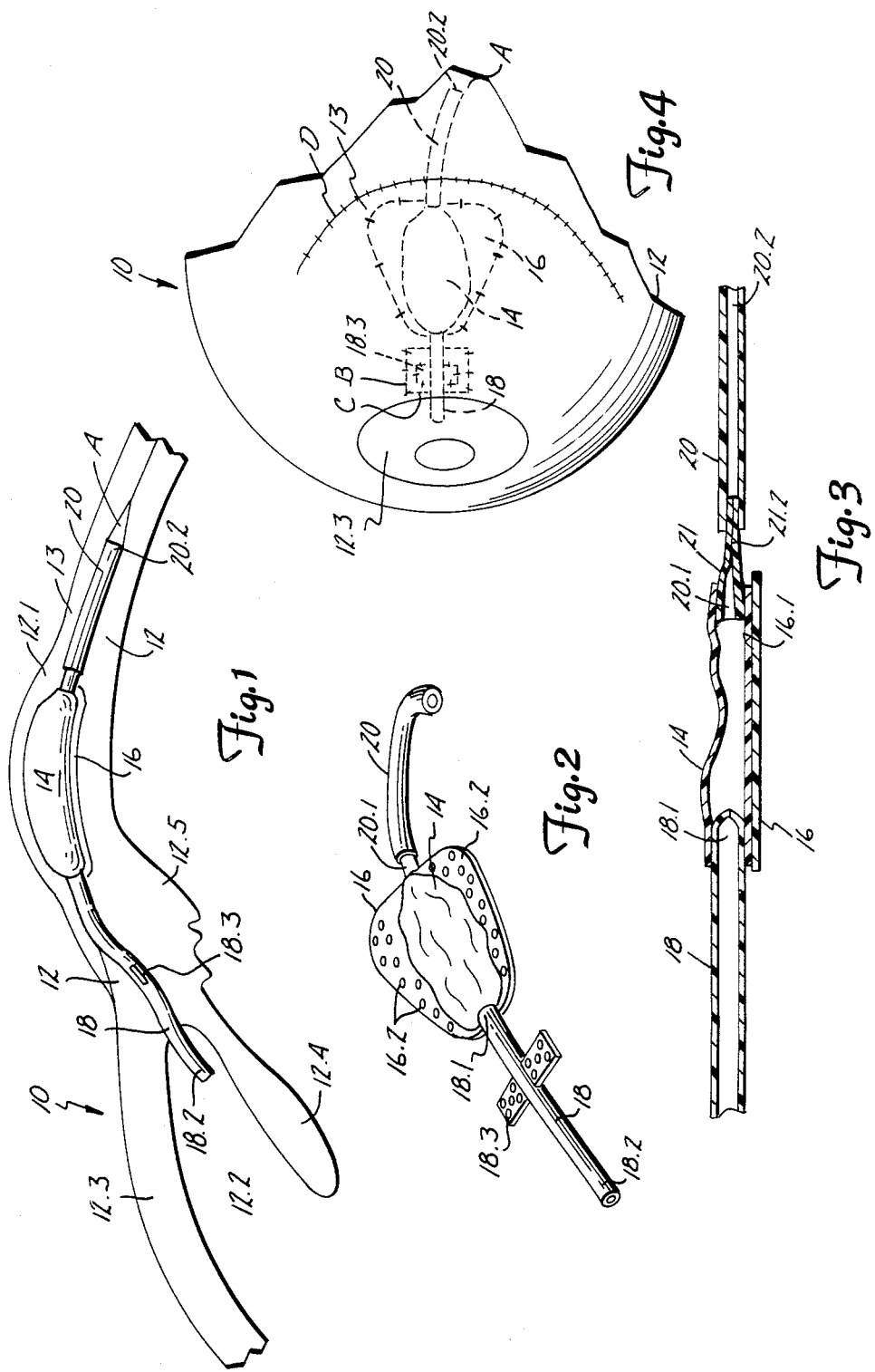

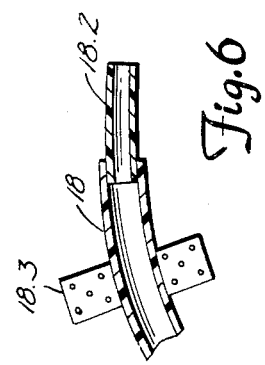
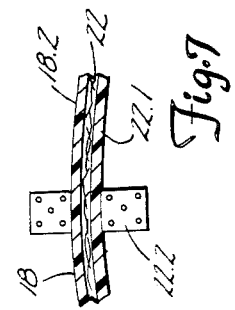
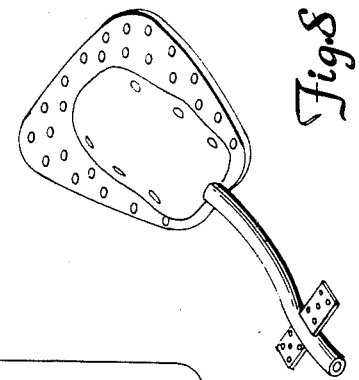
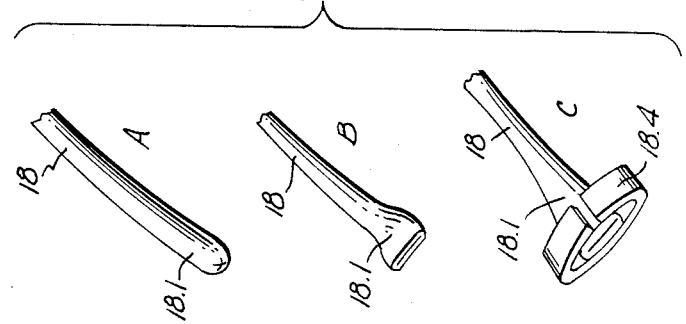

OCULAR PRESSURE RELIEF DEVICE

FIELD OF THE INVENTION

The invention relates to the field of ophthalmology, and particularly to devices and methods for the relief of unusually high interocular pressures characteristic of the disease of glaucoma.

BACKGROUND OF THE INVENTION

Glaucoma is a disease characterized by elevated intraocular pressure which, if not checked, may lead to nerve damage and visual loss. Pressures in the range of from about 15±3 mm. Hg. up to about 21 mm. Hg. may be considered to be in the normal range for human beings, whereas pressures substantially above that range are considered abnormally high. If pressures in the higher range are maintained for substantial periods of time, damage to the optic nerve of the eye may occur, leading to a narrowing of the field of vision and eventually to blindness if not appropriately treated. Although in certain cases glaucoma can be treated through the administration of certain medicines such as pilocarpine, epinephrine and timololmaleate, it is often necessary to surgically provide for the release of intraocular pressure for those patients who do not respond to drug therapy or who continue to lose vision under therapy.

Medical researchers have investigated a number of methods for the surgical release of intraocular pressure. Such surgery, in its simplest form, has involved making a small, surgical incision into the anterior chamber at or near the limbus so as to provide means for releasing an overabundance of aqueous humor from the eye into an adjacent subconjunctival space and thus to lower the intraocular pressure. In a modification of this procedure, a hair or other wicking material reported to have been placed in the incision to provide a continuous passageway for excess fluid to be discharged from the eye. Other researchers have implanted small tubes that extend through the eye wall at the limbus or scleral-corneal junction for the purpose of providing a channel through which aqueous humor can escape. Such surgical procedures, although still used to some extent, are far from adequate. Healing of the eye frequently results in scarring of the posterior drainage opening. When this occurs, no liquid may flow through the eye wall, and the intraocular pressure may rise to dangerous levels.

An excellent account of the history of glaucoma surgery is found in Bick, *Use of Tantalum for Ocular Drainage*, Archives of Ophthalmology 42:373-388 (1949).

In a recent embodiment, the exterior end of a tube extending through the wall of the eye is provided with a pressure relief valve in the form of small slits made through the wall of the tube at its end. Reference is made to Krupin, T., et al, *Valve Implants in Filtering Surgery*, Am. J. Ophthmol. 81:232-235, 1976. It is reported that fairly close control over the pressure needed to open the valve may be obtained. If the exterior or distal end of the tube is inserted beneath a flap of conjunctiva or the like, of course, the valved tube is subject to the same darwbacks as the other tubes described above.

There is thus a need in the medical field for a mechanical device which operate substantially on a continuous basis to permit excess aqueous humor to drain from the eye but would not be subject to the drawbacks associated with healing and scarring of tissue.

BRIEF DESCRIPTION OF THE INVENTION

The invention provides a prosthetic device for the relief of high intraocular pressures associated with glaucoma. The device includes a limp, expandable reservoir adapted to lie within or adjacent the exterior eye surface, a proximal conduit having one end extendable into the anterior chamber of the eye and having its other end in communication with the reservoir, unidirectional flow means restraining liquid flow within the proximal conduit to a direction toward the reservoir, and means for communicating the reservoir with liquid-receptive tissue. The latter means desirably comprises a distal conduit communicating the reservoir with liquid-receptive tissue. Such tissue includes the tissue bounding sub-conjunctival spaces or "blebs," veins and venous complexes, etc.

When the device of the invention is surgically attached to the eye, eye fluid may escape into the reservoir through the first conduit. The limp reservoir itself can be manipulated by the fingers directly or through the eyelids, or by the force of the eyelids themselves, to increase the pressure in the reservoir and thus to cause the fluid therein to be expelled under a pressure higher than the normal intraocular pressure through the distal conduit. Digital manipulation of the reservoir in this manner by a patient provides the necessarily high reservoir pressure needed to express eye fluid outwardly through the distal conduit into the surrounding tissue and to prevent that conduit from being blocked or plugged by healing or scarring of the adjacent tissue.

The proximal conduit may take the form of a fibrous wick. In the preferred embodiment, however, the proximal conduit is in the form of a small tube having exterior fastening means along its length for positively fastening the tube to the wall of the eye, preferably beneath the conjunctiva or beneath a scleral flap. At or adjacent its connection to the reservoir, the proximal conduit preferably includes a check valve permitting fluid flow only from the anterior chamber into the reservoir and preventing back flow. The check valve preferably is also a pressure relief valve which is adapted to open when the pressure in the eye exceeds the pressure in the reservoir by a pre-set threshhold pressure, e.g., by about 8-10 mm. Hg. The reservoir, being preferably of a limp material, will be maintained at or near atmospheric pressure (about 760 mm. Hg.). The distal conduit desirably is also provided with a check valve permitting only unidirectional flow through it from the reservoir and serves as a conduit for the release of fluid from the reservoir when the reservoir is pressurized by digital manipulation, such manipulation causing the pressure in the reservoir to substantially rise and to force fluid from the reservoir through the second conduit into the surrounding tissue.

DESCRIPTION OF THE DRAWING

FIG. 1 is a broken-away, schematic representation of an eye showing the positioning therein of a device of the invention;

FIG. 2 is a perspective view of a device of the invention.

FIG. 3 is a broken-away, cross-sectional view of the device of FIG. 2;

FIG. 4 is a schematic representation, broken-away, of a portion of the human eye showing steps in the surgical implantation procedure;

FIGS. 5A, B and C are broken-away, perspective views of elements of a device of the invention;

FIG. 6 is a broken-away, cross-sectional view of a modified element;

FIG. 7 is a broken-away, cross-sectional view of another modified element; and

FIG. 8 is a perspective view of another embodiment of the invention.

DETAILED DESCRIPTION

In the drawing, a section of the human eye is shown generally at (10), the scleral portion being shown at (12) and the overlying conjunctiva and Tenon's Capsule together designated (12.1). The anterior chamber is designated (12.2), and is filled with aqueous humor, a watery fluid. The cornea is designated (12.3), the iris (12.4) and the ciliary body (12.5); other structural portions of the eye have been omitted from the drawing.

A reservoir (14), having a capacity of about 20-100 microliters, is positioned against or adjacent the outer surface (12.4) of the sclera (12) beneath the conjunctiva and Tenon's Capsule (12.1) preferably in surface-to-surface contact with the sclera. The reservoir, a sac or pouch-like member desirably made of silicone rubber or latex, preferably is generally oval or disc-shaped and has thin, limp, easily deformable walls (14.1). The length and width dimensions of the reservoir may be in the range of a centimeter or smaller. If desired, the reservoir, may have one or more rigid side wall portions. It is required, however, that the reservoir be easily and readily compressed by finger pressure or other pressure source, and that the reservoir be limp; that is, it does not resiliently regain its shape. In one embodiment, an attachment plate, shown generally as (16), is provided and the reservoir is cemented or otewise attached to the outer surface (16.1) of the attachment plate. The plate itself may be of silicone rubber, polymethyl methacrylate polymer or other acceptable polymer, inert metal such as gold, or other convenient and biologically acceptable material, and the inner surface of the plate, which is generally of a spherical segmental shape, rests against and may be fastened to the scleral wall by sutures or other means. The plate may have perforations (16.2) to receive sutures and/or to permit tissue ingrowth.

A proximal conduit, represented by the tube (18), has an end portion (18.1) which passes through the wall of the reservoir (14) and is securely sealed to the reservoir. The other end portion (18.2) of the tube is adapted to be inserted through a small incision made in the wall of the eye so that the end (18.2) is positioned in the anterior chamber (12.2). The tube (18), which may be on the order of about 1 to about 3 mm. long and about 0.4 to about 1.0 mm. in outer diameter, is provided with outwardly extending fins (18.3) for attachment of the tube to the eye wall. As shown in the drawing, the fins (18.3) may be attached to the sclera beneath a thin scleral flap (12.6) as by first surgically reflecting a scleral flap adjacent the limbus, installing the tube with or without sutures that pass through or around the fins, and then sewing the flap back in place. The end portion (18.2) received in the anterior chamber may be of a comparatively rigid material such as polymethyl methacrylate or of a metal such as gold and may be joined to the reservoir by a more flexible length of, e.g., silicone rubber tubing (FIG. 6).

In the embodiment shown in FIG. 5, the end (18.1) of the conduit (18) is provided with a small slit or slits which, as shown, may be in the shape of a cross, the slits functioning as a unidirectional check valve and pressure relief valve to admit fluid from the conduit into the reservoir (14) when the pressure of fluid inside the anterior chamber reaches a predetermined value; i.e., when the pressure of fluid in the anterior chamber, and hence in the conduit exceeds the pressure in the reservoir by a predetermined amount. As shown in the above-identified Krupin, et al. article, the pressure at which the valve will open is dependent upon the nature of the slits. It has been found that by judicially forming the slits, the desired opening pressure can be controlled within the range of about 8 to about 15 mm. Hg.

A distal conduit, designated (20), has one end (20.1) that passes through and is sealed to the reservoir (14) so as to receive liquid (aqueous humor) from the reservoir. The tube (20), which may be of the same material as the tube (18), may be on the order of about 1 to about 4 mm. in length and may have an outer diameter of about 0.4-1.0 mm. The end (20.2) of the conduit (20) is positioned in contact with liquid-absorbing tissue. As shown in the drawing, a flap (13) of conjunctiva has been lifted and the end (20.2) of the tube has been inserted beneath the flap, the flap then being sewn back into place. This procedure creates a wound area or "bleb" designated "A" in the drawing, into which liquid may drain. The end (20.2) of the tube may, of course, be imbedded in other tissue, veins, etc., particularly in a vortex vein.

The conduit (20) preferably includes a unidirectional check valve to permit the conduit to carry liquid only away from the reservoir. In FIG. 3, this valve is shown as a flap valve (21.2) formed by the protrusion of short conduit length (21) within the nearer end of conduit length (21.1), the protruding end being flattened within the conduit length (21.1) and the inner surfaces of the protruding end thus being in contact with one another to permit liquid flow in one direction (to the right in FIG. 3) only.

The check valves (18.1), (21.2) may be of any of the various types suitable for use in the quite miniature device of the invention, and such valves often also function as pressure relief valves as well. As will now be understood, the function of the check valve (18.1) is to prevent the flow of aqueous humor from the reservoir back into the anterior chamber when the reservoir is pressurized as by being pressed by the fingers. When the reservoir is not so pressurized, of course, the normal pressure gradient across the valve of, e.g., 10 mm. Hg. will prevent such back flow.

FIG. 5A shows a check valve which, as explained above, also functions as a pressure relief valve, the edges of the cross-shaped slits pressing against one another to restrain fluid flow until the pressure differential across the valve increases to a valve sufficient to cause the edges to separate slightly and permit fluid to pass. Reversal of the pressure gradient, as when the reservoir is squeezed, causes the edges of the slits to press more tightly together, further restricting flow. A similar principle of operation is employed by the valve of FIG. 5B, in which the end (18.1) of the conduit is slit axially for a short distance to provide flaps (shown also in the valve (21.2) of FIG. 3). A spring of metal or other springy material as shown at (18.4) of FIG. 5C may additionally be employed to squeeze shut the end of the conduit (18) to provide a pressure relief function. Various other miniaturized valves, such as ball valves and the like, may be employed.

It will be understood that only a very small amount of aqueous humor, e.g., about 20 to about 100 microliters, must be removed from the eye daily in order to maintain the internal pressure of the eye at a reasonably constant, normal level.

Once the device of the invention has been surgically attached, aqueous humor will pass into the reservoir (14) through the conduit (18) when the pressure differential between the anterior chamber of the eye and the interior of the reservoir exceeds a predetermined level. For example, if the internal eye pressure is to be maintained at or below about 20 mm. Hg. (which is, in fact, a "gauge" pressure, or pressure above atmospheric pressure), then the pressure relief valve should be set to open at a pressure differential of 20 mm. Hg. or below. As the reservoir slowly fills, little if any drainage will occur through the conduit (20). However, when the reservoir is compressed, as when a patient performs a simple finger massage of the eye, preferably through the eyelid, or by forced eyelid pressure itself, the pressure within the reservoir (14) is increased to force fluid through the conduit (20). The pressure that is generated within the reservoir may be in the range of about 25 to about 45 mm. Hg., and in any event is sufficient to overcome the effects of healing or scarring in the area "A" and to retain the area "A" receptive to the absorbence of eye fluid. That is, the pressure of fluid passing through the distal conduit (20) is sufficiently high as to substantially prevent healing of the area "A" in a manner limiting the ability of the tissue to receive and absorb fluid.

If the reservoir is layed directly against the globe, then the additional pressure within the reservoir generated by finger massage will be transmitted directly to the anterior chamber, raising the anterior chamber pressure and reducing the likelihood of reverse flow of eye flow through the conduit (18). If the reservoir (14) is mounted upon a mounting plate such as that shown as (16) in FIG. 2, and assuming that the area of contact of the mounting plate with the surface of the eye is greater than the area of contact between the mounting plate and the reservoir, then, applying simple hydraulic principles, the increase in pressure within the eye will be somewhat less than the pressure developed in the reservoir, permitting greater reservoir pressures to be developed.

In another embodiment, the proximal conduit (18) may take the form of a porous material which may consist of one or a plurality of fibers, optionally interwoven, which serve as a wick for the passage of aqueous humor. In one such embodiment, shown in FIG. 4, the wick (22) is shown encased in a short tubular section (22.1) similar to that shown at (18) in FIG. 3. The tube optionally additionally includes fins (22.2) or other means for attachment of the tube to the eye wall. The tubular section (22.1) is provided for the purpose of maintaining reasonable sterile conditions and to insure that all of the eye fluid passing from the interior of the eye is directed into the reservoir (14) from which it can be expressed, by manual massage, through the second conduit (20). The flow rate of aqueous humor through the wick may be adjusted to some extent by judicious selection of the wicking material, the diameter of the tubular section (22.1), etc. The outward flow of liquid from the eye to the reservoir (14) thus occurs gradually. When the reservoir is subjected to momentary digital massage or forced eyelid massage, little if any liquid passes in the reverse direction through the wick (22) because of the normal resistance of the wick to the rapid flow of fluid.

The end (20.2) of the conduit (20) may, in one embodiment, be connected to a vortex vein of the eye so that aqueous humor from the reservoir is discharged into the veinous system. Since the normal pressure in the vortex veins is on the order of 10 mm. Hg., and since this pressure is not abnormal as an intraocular pressure, the valve at (18.1) (FIG. 3) may be merely a check valve permitting unidirectional fluid flow into the reservoir at negligable pressure differentials. In this embodiment, the pressure downstream of the valve normally would be about the same as the venous pressure in the vortex vein, and the flow of aqueous humor through the valve at (18.1) would occur only when the intraocular pressure exceeded the venous pressure.

Another embodiment of the invention is shown in FIG. 8 and is identical to that described above in connection with FIGS. 1-3 except that the means communicating the reservoir (14) with liquid receptive tissue comprises slits or holes formed in the walls of the reservoir itself. When squeezed, as by finger massage, the reservoir expels aqueous humor within the subconjunctival space in which it is implanted.

With reference to FIG. 4, one surgical procedure involves making an incision, shown at "D", through the conjuctiva and Tenon's Capsule, and reflecting these layers upon the cornea (12.3) to expose the scleral surface. A scleral flap "B" is then lifted adjacent the limbus and a small incision is made into the anterior chamber at "C". The end (18.2) of the proximal conduit is inserted through this incision into the anterior chamber, the fins (18.3) are buried beneath the scleral flap with or without sutures, and the flap "B" is sutured back in place as shown, the conduit (18) extending posteriorly onto the exposed scleral surface. The mounting plate (16) is sutured onto the scleral surface to anchor the reservoir (14), and the end (20.2) of the distal conduit is imbedded in a surgically prepared subconjunctival space or attached within the lumen of a vortex vein or otherwise disposed within liquid receptive tissue. The reflected flap is then sutured back in place, completing the surgical portion of the procedure.

It will now be appreciated that the primary purpose of the reservoir 14 is to provide means for expressing aqueous humor into receptive tissue, veins, etc. under comparatively high pressures, thereby overcoming resistance to flow arising from scarring of the otherwise receptive tissue or blockage of the distal conduit (20) by clots or the like. In its broader form, accordingly, the device includes a limp, expandable reservoir including means communicating the reservoir with liquid receptive tissue, a conduit communicating with the reservoir and having an end insertable in the anterior chamber of the eye, and unidirectional valve means permitting the flow of liquid through the conduit solely toward the reservoir.

While a preferred embodiment of the present invention has been described, it should be understood that various changes, adaptations and modifications may be made therein without departing from the spirit of the invention and the scope of the appended claims.

What is claimed is:

1. A prosthetic device for the relief of high intraocular pressure associated with glaucoma comprising:
   (a) a limp, expandable, compressible reservoir adapted to be positioned within or adjacent to the exterior eye surface; said reservoir being constructed so that when so positioned, said reservoir does not resiliently regain its shape and is maintained at about atmospheric pressure;

(b) a proximal conduit having one end extendable into the anterior chamber of the eye and fastenable to the wall of the eye, and having its other end in communication with said reservoir whereby eye fluid may escape into said reservoir;

(c) unidirectional flow means restraining liquid flow within said proximal conduit to a direction toward said reservoir; said flow means further including pressure relief means adapted to open when the pressure in the eye exceeds the pressure in said reservoir by a pre-set threshold pressure; and (d) means communicating said reservoir with surrounding liquid-receptive tissue and having valve means permitting only unidirectional flow therethrough, whereby said reservoir may be manipulated to a high reservoir pressure needed to expel eye fluid outwardly therefrom through said distal conduit.

2. The device of claim 1 wherein said unidirectional flow means comprises a pressure relief valve in the proximal conduit for permitting said unidirectional flow of aqueous humor when the pressure differential across the valve increases to a predetermined level.

3. The device of claim 1 wherein said means for communicating the reservoir with liquid-receptive tissue comprises a distal conduit communicating at one end with the reservoir and its other end being adapted for communication with liquid receptive tissue.

4. The device of claim 1 including a mounting plate carried by the reservoir and curved to fit snugly against or within the eye wall, with a surface contact area greater than the surface contact area between the reservoir and the plate.

5. The device of claim 3 wherein said distal conduit includes check valve means restraining liquid flow to a direction away from the reservoir.

6. The device of claim 1 wherein said proximal conduit comprises a length of tubing and wherein said unidirectional flow means comprises a wick carried within the tubing.

7. A prosthetic device for the relief of high intraocular pressure associated with glaucoma comprising:

(a) a limp, expandable, compressible reservoir having a capacity of about 20–100 microliters and adapted to be positioned within or adjacent to the exterior eye surface; said reservoir being constructed so that when so positioned, said reservoir does not resiliently regain its shape and is maintained at about atmospheric pressure;

(b) a proximal conduit having one end extendable into the anterior chamber of the eye and fastenable to the wall of the eye, and having its other end in communication with said reservoir whereby eye fluid may escape into said reservoir, and said conduit having an outer diameter of about 0.4 to 1.0 mm;

(c) unidirectional flow means restraining liquid flow within said proximal conduit to a direction toward said reservoir; said flow means further including pressure relief means adapted to open when the pressure in the eye exceeds the pressure in said reservoir by a pre-set threshold pressure; and (d) means communicating said reservoir with surrounding liquid-receptive tissue and having valve means permitting only unidirectional flow therethrough, whereby said reservoir may be manipulated to a high reservoir pressure needed to expel eye fluid outwardly therefrom through said distal conduit.

8. A method of treating a patient having elevated intraocular pressure comprising:

(a) surgically attaching to the eye of the patient a pressure relief device having a limp, expandable reservoir, a proximal conduit communicating with the reservoir and including a unidirectional flow means, and a distal conduit, also communicating with the reservoir, comprising the steps of:

(i) securing the reservoir to the eye so that the reservoir may be compressed by manual pressure;

(ii) inserting the proximal end of the proximal conduit into the anterior chamber of the eye; and (iii) locating the distal conduit in liquid receptive tissue; and (b) compressing the reservoir from time to time to expel accumulated aqueous humor.

9. The method of claim 8 wherein the securing step includes steps of making an incision through the conjunctiva and Tenon's Capsule of the eye to expose the scleral surface, and suturing the reservoir to the scleral surface.

10. The method of claim 8 wherein the locating step includes placing the distal conduit in a surgically prepared subconjunctival space.

11. The method of claim 8 wherein the locating step includes placing the distal conduit in the lumen of a vortex vein.

12. The method of claim 8 wherein the compressing step includes digital manipulation of the reservoir through the eyelid.

13. The method of claim 8 wherein the compressing step includes blinking the eyelid.

* * * * *